US00PP31127P2

(12) United States Plant Patent
Hansen

(10) Patent No.: US PP31,127 P2
(45) Date of Patent: Nov. 26, 2019

(54) ***NEPETA* PLANT NAMED 'CAT'S PAJAMAS'**

(50) Latin Name: *Nepeta hybrid*
Varietal Denomination: Cat's Pajamas

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/998,378

(22) Filed: Aug. 10, 2018

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
CPC ..... A01H 6/00; A01H 5/02
See application file for complete search history.

*Primary Examiner* — Keith O. Robinson

(57) ABSTRACT

The new and distinct hardy perennial plant, *Nepeta* 'Cat's Pajamas', has rounded, short and compact habit with mostly upright to outwardly stems. The foliage is cordate, serrate to crenate. Flowers are a strong violet color with moderate-purple, persistent calyces beginning as much as two weeks prior to other Catmint. The new plant is useful in the landscape en masse, as an accent, or in containers.

1 Drawing Sheet

Botanical denomination: *Nepeta* hybrid.
Variety designation: 'Cat's Pajamas'.

BACKGROUND OF THE INVENTION

The present invention relates to a new and distinct cultivar of *Nepeta* named 'Cat's Pajamas'. The new plant resulted from a cross between *Nepeta faassenii* 'Purrsian Blue' U.S. Plant Pat. No. 24,788 as the female or seed parent and a proprietary unnamed selection of *Nepeta phylloclamys* (non-patented) as the male or pollen parent on Jun. 6, 2013. Seed was harvested in the summer of 2013 and given the breeder code 13-13-5 during the final trial stages of the summer of 2015. The new plant was selected based on the early blooming and compact habit traits. The new plant has been asexually propagated by division in 2015 and shoot tip cuttings since the spring of 2016 with the resultant plants remaining identical to the original plant, stable and true to type in successive generations.

SUMMARY OF THE INVENTION

*Nepeta* 'Cat's Pajamas' is different from its parents and all other Catmint known to the inventor. In comparison to the female parent, *Nepeta* 'Purrsian Blue', the new plant is shorter and more compact and begins blooming about two weeks earlier and stays in bloom longer. 'Purrsian Blue' is also larger in width and the flowers are slightly lighter in hue than the new plant. 'Cat's Pajamas' flowers on nodes from the soil line to the apex. Compared with the male parent, the new plant is taller, has less gray and more green foliage and flowers for a longer period. The male parent has more silvery foliage, is more compact in habit, and the flowers are smaller. The nearest comparison variety is *Nepeta* 'Novanepjun' U.S. Plant Pat. No. 23,074 more commonly known as 'Junior Walker'. 'Cat's Pajamas' is shorter and narrower in habit than 'Novanepjun', and the new plant flowers for a longer period of time. 'Psfike' U.S. Plant Pat. No. 18,904 is slightly shorter in habit. 'Purple Haze' U.S.

Plant Pat. No. 23,180 is slightly shorter, less compact, more trailing in habit, less winter hardy with more villous calyces. 'Cat's Meow' U.S. Plant Pat. No. 24,472 is much taller and broader in habit than the new plant. 'Kitten Around' U.S. Plant patent application Ser. No. 15/732,459 most notably has smaller foliage and slightly smaller habit and begins flowering about two weeks later than the new plant.

The present invention has not been evaluated under all possible environmental conditions. The phenotype may vary with changes in the environment such as light, temperature, water and nutrient availability, etc. without a change in the genotype of the plant. *Nepeta* 'Cat's Pajamas' is unique from all other Catmint known to the inventor in the following combined traits:

1. The habit is rounded, short and compact with mostly upright to slightly outright stems.
2. Foliage is cordate, small and serrate to crenate with slightly rounded teeth.
3. Flowers are strong violet and persistent moderate-purple calyces.
4. Flowers beginning earlier and repeats better when trimmed back than many other *Nepeta faasseni* cultivars.

BRIEF DESCRIPTION OF THE DRAWINGS

The photographs of the new plant *Nepeta* 'Cat's Pajamas' are of a three-year old plant in a full sun trial garden in Zeeland, Mich. and demonstrate the unique aspects of the new plant. The colors are as accurate as reasonably possible with color reproductions. Ambient light spectrum, temperature, source and direction may cause the appearance of minor variation in color.

DETAILED PLANT DESCRIPTION

Figure 1:
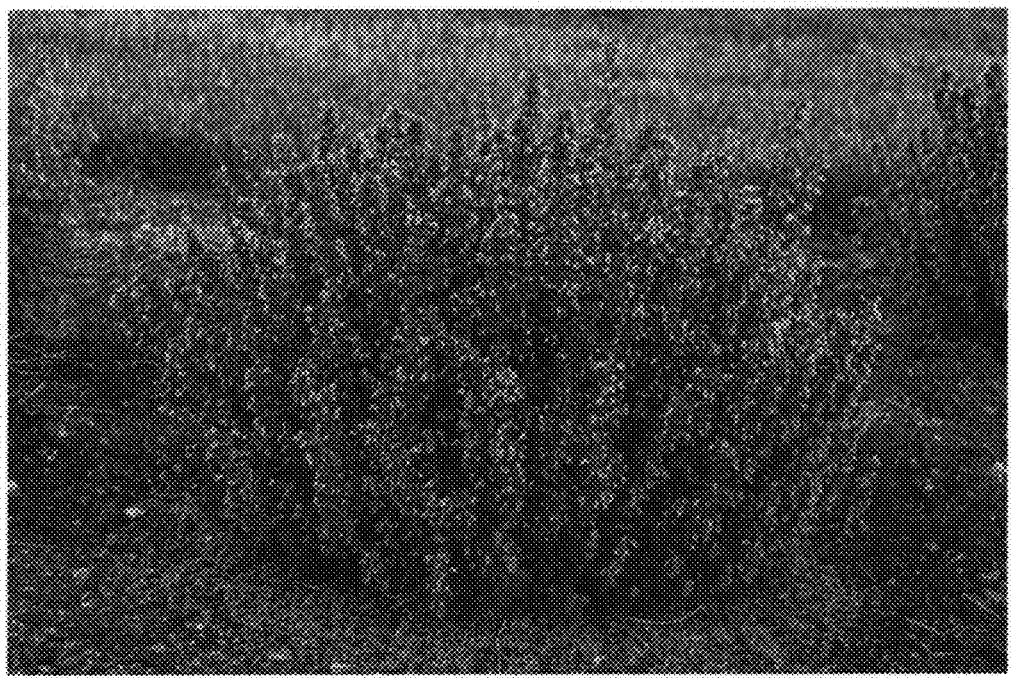
FIG. 1 shows the overall habit of *Nepeta* 'Cat's Pajamas'.
Figure 2:
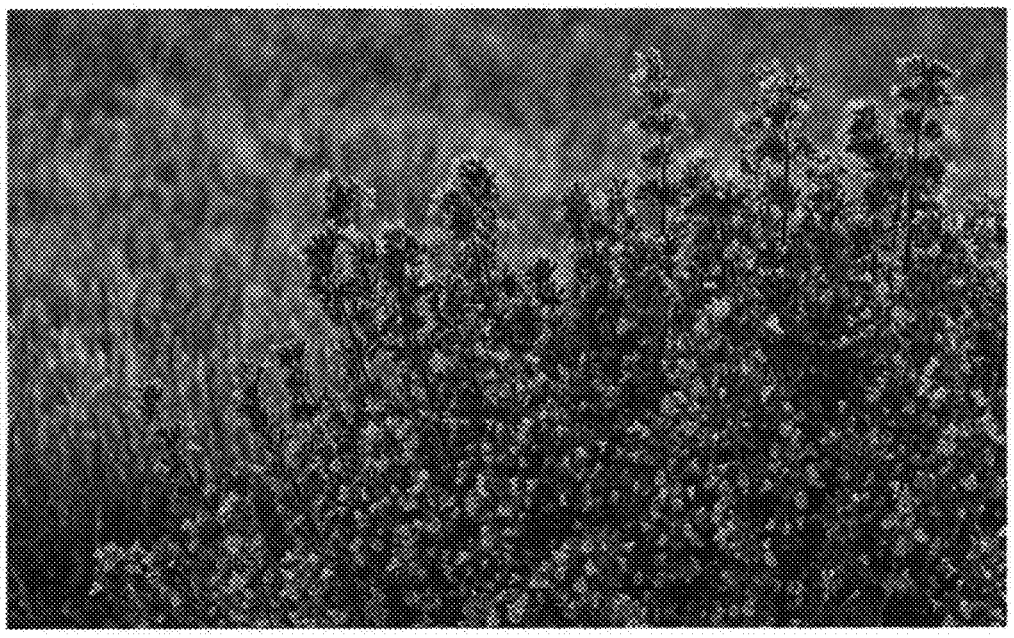
FIG. 2 shows a close-up of the flower.

The following descriptions are based on a two-year old plant of *Nepeta* 'Cat's Pajamas' grown in a full-sun display garden in sandy loam with supplemental water and fertilizer as needed. The color references are based on the 2015 edition of The Royal Horticultural Society Colour Chart except where common dictionary terms are used. The new plant has not been observed under all possible environments. The phenotype may vary slightly with different environmental conditions, such as temperature, light, fertility, moisture and maturity levels, but without any change in the genotype.

Parentage: *Nepeta faassenii* 'Purrsian Blue' (female, seed), proprietary unnamed selection of *Nepeta phylloclamys* (male, pollen);

Plant habit: Herbaceous perennial; upright mounding to about 28 cm tall and 46 cm wide at the soil level when in peak flower;

Growth: Rapid; finishing in a standard #1-15 cm container in about 12 to 15 weeks from rooted plug; time to initiate roots at 23° C. about one week;

Root: Fine, freely branching; color nearest RHS 158D depending on soil type and nutrient content;

Foliage: Opposite, simple, cordate; rugose on adaxial surface, with ribbed vein on abaxial surface; margins serrate to crenate with slightly rounded teeth; micro-villosulous on abaxial and adaxial surfaces; apex broadly acute; base rounded; blade size about 12.0 mm long and 13.0 mm wide;

Venation: Longitudinal; impressed on adaxial surface and ribbed on abaxial surface;

Vein color: Nearest RHS 147C on adaxial surface and nearest RHS 147C on abaxial surface;

Leaf color: Adaxial surface nearest RHS 137B, abaxial surface between RHS 147C and RHS 147B;

Petiole: Micro-villosulous on abaxial and adaxial surfaces; about 3.0 mm long and 2.0 mm diameter in basal region of stem decreasing in size to nearly sessile in distal region;

Petiole color: Nearest RHS 147C adaxial and between RHS 148B and RHS 148C abaxial;

Stem: Micro-puberulent; quadangular, about 2.0 mm across at base and to about 34.0 cm long; mostly upright to slight outwardly;

Internodes: Average about 19.0 mm apart with greatest distance in the middle of the stem; about 18 nodes per stem;

Stem color: Nearest RHS 138A with strong tinting in high sun exposure nearest RHS N186C; node color normally same as surrounding stem;

Inflorescence: Cymosely clustered with many flowers oppositely branched or stalked at nodes; about 6 to 42 flowers per node and about 184 per inflorescence stem or peduncle;

Inflorescence season: For about eight weeks beginning in early May;

Stalks: Terete to quadrangular; uprightly; micro-puberulent; to about 10.0 mm long and 0.5 mm diameter, decreasing distally; color nearest RHS 138A to strongly tinted with nearest RHS N186C;

Peduncle: Main stem mostly vertical to about 32 cm tall with flowers on the distal 16 cm;

Pedicel: Sessile;

Flower bud: Curved clavate; about 9.0 mm long and 3.5 mm wide at the widest point one day prior to opening; adaxial calyx surface puberulent; slightly arcuate;

Flower bud color: Petal portion nearest RHS 90C, calyx portion nearest blend between RHS 138C and RHS 146D with strong tinting of nearest RHS 83C;

Flowers: Zygomorphic; bilabiate; about 10.0 mm long and about 5.0 mm wide at lip; sympetalous with basal 5.0 mm fused; bisexual or lacking androecium; synsepalous; slightly arcuate;

*Upper lip*.—Micro-puberulent on abaxial surface, glabrous on adaxial surface; emarginate apex and fused base; dorsally flattened parallel to peduncle, about 10.0 mm long and about 3.0 mm across at widest portion; adaxial color nearest RHS 83C; abaxial color nearest RHS 90C.

*Lower lip*.—Consisting of three fused lobes, micro-puberulent on abaxial in basal tube and center portion, glabrous distal portion; pubescent in center adaxial portion and glabrous in basal and distal adaxial portion; center lobe apex crenate and curled, base fused; distally to 7.0 mm across, two side lobes to 2.0 mm across; center lobe adaxial color nearest blend between RHS 90B and RHS 86A distally with dark spots nearest RHS 90A in center portion; center lobe abaxial color nearest RHS 90A; side lobe adaxial color nearest RHS 83C, side lobe abaxial color nearest RHS 90C.

*Tube*.—Fused in about basal 5.0 mm, to about 1.0 mm base and flaring to about 2.0 mm before split; color adaxial base lighter than RHS 85D and distally nearest RHS 85C maculate with spots about 0.3 mm diameter of nearest RHS 90A; color abaxial base lighter than RHS 85D, distally nearest RHS 85A.

*Calyx*.—Synsepalous, 5-merous fused into calyx tube in basal 5.0 mm and separated in distal 1.0 mm; acute apex, base fused; with about 15 conspicuous ribs; puberulent abaxial, glabrous adaxial; persistent; about 6.5 mm long and 2.0 mm diameter; adaxial so color blend between RHS N148D and RHS 145C with darker ribs of RHS 147B and tinted distally nearest RHS N186C; abaxial color nearest blend between RHS N148D and RHS 145C between veins with veins nearest RHS 147B, tinted in region getting direct sunlight nearest RHS N186C.

*Gynoecium*.—Single compound ovary with two carpels, single gynobasic style, and stigma split in two parts; style arcuate, about 9.5 mm long and 0.3 mm diameter, style color nearest RHS 83D; stigma bifid in last 0.5 mm with sharply acute apex, stigma color nearest RHS 83A; ovary four-lobed, each lobe ovoid, about 0.7 mm long and 0.7 mm across, ovary color nearest RHS 145A.

*Androecium*.—Anthers, filaments and pollen not observed under some conditions or only two stamens that are adnate to the inner corolla tube; when present anthers not developed, no pollen observed; filaments when present about 1.0 mm long and less than 0.3 mm diameter; filament color whiter than RHS NN155B; stamen when present ovoid, about 1.0 mm long and 0.5 mm diameter; stamen color between RHS N187B and RHS 187A.

Flowering period: Late spring into early fall in West Michigan when trimmed after initial flowering; individual flowers remain open for up to three days;

Fragrance: Foliage and stem herbal almost minty fragrance; no fragrance detected from flowers;

Fruit and seed: Rare, outlets, flattened, round; about 1.5 mm diameter and 0.5 mm thick; nearest RHS 200B;

Pest and disease susceptibility: No resistance beyond that which is typical for *Nepeta* but typically not prone to browsing by deer or rodents. The new plant has not been found to be susceptible to bacterial or fungal leaf spots.

Hardiness: Hardy from USDA zones 3 through 8;

I claim:

1. The new and distinct hardy perennial plant, *Nepeta* 'Cat's Pajamas' essentially as herein described and illustrated.

* * * * *